United States Patent
Adhiprakasha et al.

(10) Patent No.: US 9,297,775 B2
(45) Date of Patent: Mar. 29, 2016

(54) COMBINATORIAL SCREENING OF METALLIC DIFFUSION BARRIERS

(71) Applicant: Intermolecular Inc., San Jose, CA (US)

(72) Inventors: Edwin Adhiprakasha, Mountain View, CA (US); Sean Barstow, San Jose, CA (US); Ashish Bodke, San Jose, CA (US); Zhendong Hong, San Jose, CA (US); Usha Raghuram, Saratoga, CA (US); Karthik Ramani, Santa Clara, CA (US); Vivian Ryan, Berne, NY (US); Jingang Su, Cupertino, CA (US); Xunyuan Zhang, Albany, NY (US)

(73) Assignee: Intermolecular, Inc., San Jose, CA (US)

( * ) Notice: Subject to any disclaimer, the term of this patent is extended or adjusted under 35 U.S.C. 154(b) by 0 days.

(21) Appl. No.: 14/285,921

(22) Filed: May 23, 2014

(65) Prior Publication Data

US 2015/0338362 A1 Nov. 26, 2015

(51) Int. Cl.
| | |
|---|---|
| *H01L 27/20* | (2006.01) |
| *G01N 27/20* | (2006.01) |
| *C23C 14/34* | (2006.01) |
| *C23C 14/54* | (2006.01) |
| *C23C 14/06* | (2006.01) |
| *G01N 27/04* | (2006.01) |

(52) U.S. Cl.
CPC ............... *G01N 27/20* (2013.01); *C23C 14/06* (2013.01); *C23C 14/3464* (2013.01); *C23C 14/54* (2013.01); *G01N 27/041* (2013.01)

(58) Field of Classification Search
CPC ................... H01L 21/32051; H01L 21/67207; H01L 21/6708
See application file for complete search history.

(56) References Cited

U.S. PATENT DOCUMENTS

| | | | |
|---|---|---|---|
| 6,077,779 A | 6/2000 | Shue | |
| 6,143,650 A | 11/2000 | Pramanick | |
| 6,362,526 B1 | 3/2002 | Pramanick | |
| 6,403,465 B1 | 6/2002 | Liu | |
| 6,482,734 B1* | 11/2002 | Ha et al. ........................ | 438/643 |
| 6,787,910 B2 | 9/2004 | Lee | |
| 6,800,494 B1 | 10/2004 | Castle | |
| 7,867,904 B2 | 1/2011 | Chiang et al. | |
| 8,084,400 B2 | 12/2011 | Chiang | |
| 8,575,027 B1* | 11/2013 | Barstow et al. ............... | 438/679 |
| 2007/0089857 A1* | 4/2007 | Chiang et al. ................ | 165/80.2 |
| 2007/0269611 A1 | 11/2007 | Xiang et al. | |
| 2009/0275210 A1 | 11/2009 | Shanker et al. | |
| 2010/0013096 A1 | 1/2010 | Irumata et al. | |

* cited by examiner

*Primary Examiner* — Matthew Reames

(57) ABSTRACT

Barrier layers, barrier stacks, and seed layers for small-scale interconnects (e.g., copper) are combinatorially screened using test structures sputtered or co-sputtered through apertures of varying size. Various characteristics (e.g., resistivity, crystalline morphology, surface roughness) related to conductivity, diffusion blocking, and adhesion are measured before and/or after annealing and compared to arrive at materials and process parameters for low diffusion with high conductivity through the interconnect. Example results show that some formulations of tantalum-titanium barriers may replace thicker tantalum/tantalum-nitride stacks, in some cases with a Cu—Mn seed layer between the Ta—Ti and copper.

20 Claims, 8 Drawing Sheets

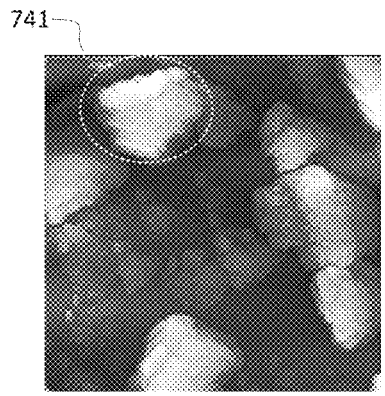
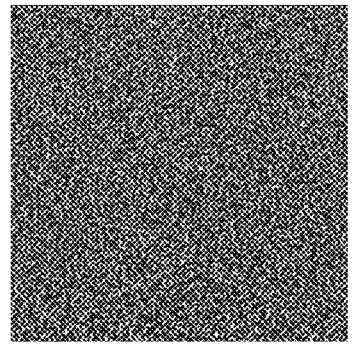
FIG. 7G    FIG. 7H
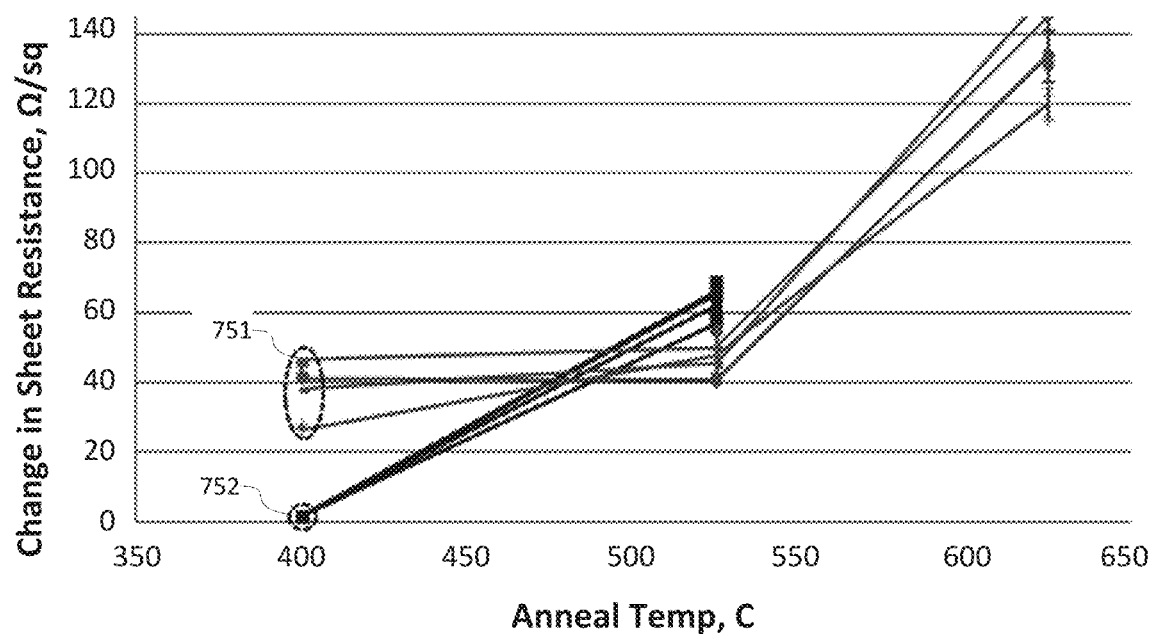
FIG. 7I

COMBINATORIAL SCREENING OF METALLIC DIFFUSION BARRIERS

BACKGROUND

Related fields include diffusion barrier layers in semiconductor devices, particularly those for blocking the diffusion of copper and oxygen.

As the feature sizes of microelectronic assemblies (e.g., integrated circuits) continue to decrease, manufacturing challenges emerge. For example, diffusion barrier layers are often used between conductive interconnects or vias, often made of copper, and the surrounding interlayer dielectric (ILD) materials, such as silicon dioxide or other insulating materials. Without the diffusion barrier, the copper may diffuse into the ILD, compromising its insulating properties; likewise, materials from the ILD, such as oxygen, may diffuse into the copper and compromise its conductive properties. Therefore, diffusion barrier layers may need to have low diffusion coefficients ($<10^{-8}$ $cm^2/s$).

As the interconnects and vias decrease in size and increase in density, the diffusion barrier layers, quite thin to begin with, must scale proportionally with the vias, trenches, and interconnects; i.e., they must become even thinner to fit in the available space. Moreover, because the smaller features are often more sensitive to contamination, such new thinner diffusion barrier layers must perform at least as well as, and preferably better than, their thicker predecessors.

Besides blocking diffusion into and out of the interconnects, these diffusion barriers preferably have low resistivity to assist the interconnect in carrying current, and good adhesion to copper so that thin copper layers do not agglomerate (become non-contiguous) when the substrate is heat-treated during processing.

A bi-layer diffusion barrier of tantalum nitride (TaN) and metallic tantalum (Ta) is presently used in many integrated circuit devices. The TaN blocks diffusion and the Ta provides an interface for copper adhesion. Copper layers thinner than about 20 nm tend to agglomerate during annealing if they are deposited directly on TaN, and Ta by itself does not sufficiently block diffusion. Both the TaN and the Ta performance degrade as the layers become thinner.

Often a thin "seed layer" will be deposited on the diffusion barrier layer before forming the interconnect. Many current devices use a copper seed layer. If the seed layer could contribute to diffusion blocking and adhesion promotion, it could relax some of the demands on the diffusion barrier layer.

Therefore, a need exists for materials that block diffusion and provide adhesion for copper at smaller thicknesses. If a single layer of material could provide both diffusion blocking and adhesion, it would simplify manufacturing and reduce cost. If a seed layer could perform an extra function of diffusion blocking or adhesion promotion, it would allow diffusion barrier layers to be even thinner, and/or to be eliminated completely.

SUMMARY

The following summary presents some concepts in a simplified form as an introduction to the detailed description that follows. It does not necessarily identify key or critical elements and is not intended to reflect a scope of invention.

Embodiments of methods for screening candidate materials and processes for barrier layers make use of High Productivity Combinatorial (HPC) approaches. Successful candidate barrier layers (or barrier stacks) for interconnects have low diffusion coefficients for both the interconnect material (e.g., copper) and components of the surrounding ILD (e.g., $SiO_2$). Multiple test structures may be formed in site-isolated regions on a single substrate, with at least one process parameter varied between at least two of the test structures in a combinatorial manner. After the structures are formed, the substrate may be annealed. Characteristics of the test structures may be measured and compared before annealing, after annealing, or both. From the measurements and comparisons, one or more preferred candidate barrier layers may be selected.

The test structures may include a copper layer and a candidate barrier layer formed over a substrate. In some embodiments, the test structure may also include a dielectric layer such that the candidate barrier layer is between the dielectric layer and the copper layer. In some embodiments, the candidate barrier layer may be a stack of two or more different materials, or a material with a composition gradient. In some embodiments, a seed layer may be formed between the candidate barrier layer and the copper layer. In some embodiments, the test structure may include a second barrier layer such that the copper layer is between the two barrier layers. Parts of the test structures may be individually formed in the site-isolated regions, while other parts may be deposited as uniform "blanket" layers covering the entire substrate, or covering a portion of the substrate that does not correspond to a site-isolated region.

Process parameters to be varied between the test structures may include material composition, composition profile (e.g., gradients), layer thickness, layer order, deposition method, deposition temperature, chamber pressure, and chamber ambient gases and their flow rates.

The test structures may be formed by physical vapor deposition (PVD; e.g., sputtering). The sputtered material or the sputtering process parameters may be combinatorially varied between different test structures on the substrate. A PVD chamber equipped with multiple sputter guns may co-sputter components of compound or alloyed barrier layers or seed layers from separate targets. The targets may be sputtered at different levels or types of plasma power (e.g., DC, pulsed DC, or RF power), and may be located at different distances from, or angles to, the substrate. The power, distance, or angle of each target may be varied from one site-isolated region to another, or it may be varied while depositing a single candidate layer to produce a composition gradient.

Characteristics measured on the candidate barrier layers, copper layers, dielectrics, or substrate before or after annealing may include resistivity, uniformity, contiguity, surface roughness, chemical composition, or morphology (e.g., crystallinity). Measurement methods may include using 4-point probes or resmap tools to measure sheet or surface resistivity; X-ray fluorescence (XRF), Rutherford backscattering spectrometry (RBS), scanning electron microscopy (SEM), tunneling electron microscopy (TEM), atomic force microscopy (AFM), X-ray diffraction (XRD), or any other suitable methods of measuring electrical properties, crystalline morphology, chemical composition, and surface characteristics.

BRIEF DESCRIPTION OF DRAWINGS

The accompanying drawings may illustrate examples of concepts, embodiments, or results. They do not define or limit the scope of invention. They are not drawn to any absolute or relative scale. In some cases, identical or similar reference numbers may be used for identical or similar features in multiple drawings.

FIGS. 7A-7I are examples of results from HPC screening experiments.

DETAILED DESCRIPTION OF EXAMPLE EMBODIMENTS

Figure 1:
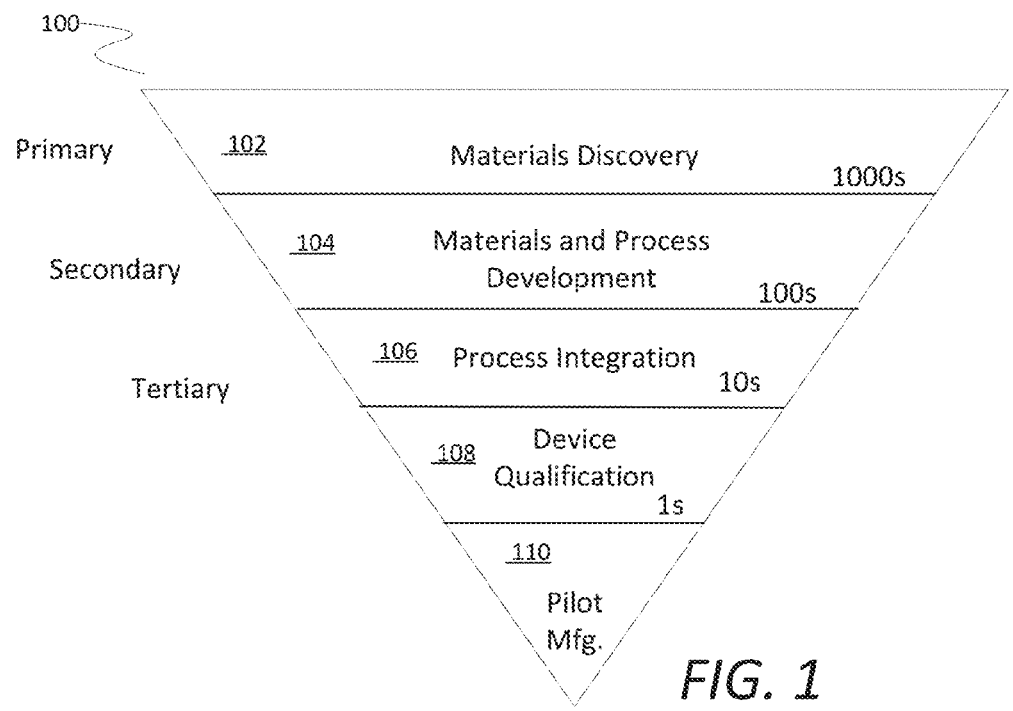
FIG. 1 is a schematic diagram of device development using primary, secondary, and tertiary screening methods that include HPC processing and may also include conventional processing.

A detailed description of one or more example embodiments is provided below. To avoid unnecessarily obscuring the description, some technical material known in the related fields is not described in detail. Semiconductor fabrication generally requires many other processes before and after those described; this description omits steps that are irrelevant to, or that may be performed independently of, the described processes.

Unless the text or context clearly dictates otherwise: (1) By default, singular articles "a," "an," and "the" (or the absence of an article) may encompass plural variations; for example, "a layer" may mean "one or more layers." (2) "Or" in a list of multiple items means that any, all, or any combination of less than all the items in the list may be used in the invention. (3) Where a range of values is provided, each intervening value is encompassed within the invention. (4) "About" or "approximately" contemplates up to 10% variation. "Substantially equal," "substantially unchanged" and the like contemplate up to 5% variation.

"Horizontal" defines a plane parallel to the plane or surface of the substrate. "Vertical" shall mean a direction perpendicular to the horizontal. "Above," "below," "bottom," "top," "side" (e.g. sidewall), "higher," "lower," "upper," "over," and "under" are defined with respect to the horizontal plane. "On" indicates direct contact; "above" and "over" allow for intervening elements. "On" and "over" include conformal configurations covering feature walls oriented in any direction.

"Substrate," as used herein, may mean any workpiece on which formation or treatment of material layers is desired. Substrates may include, without limitation, silicon, germanium, silica, sapphire, zinc oxide, SiC, AlN, GaN, Spinel, coated silicon, silicon on oxide, silicon carbide on oxide, glass, gallium nitride, indium nitride and aluminum nitride, and combinations (or alloys) thereof. The term "substrate" or "wafer" may be used interchangeably herein. Semiconductor wafer shapes and sizes can vary and include commonly used round wafers of 50 mm, 100 mm, 150 mm, 200 mm, 300 mm, or 450 mm in diameter. Furthermore, the substrates may be processed in many configurations such as single substrate processing, multiple substrate batch processing, in-line continuous processing, in-line "stop and soak" processing, or roll-to-roll processing.

As used herein, "combinatorial processing" or "combinatorial variation" shall mean that a material or process parameter is caused to differ between at least two regions of a single substrate. Such parameters include, without limitation, process material amounts, reactant species, processing temperatures, processing times, processing pressures, processing flow rates, processing powers, processing reagent compositions, the rates at which the reactions are quenched, deposition order of process materials, process sequence steps, or hardware details.

As used herein, the phrase "site-isolated region" (SIR) will be understood to refer to one or more regions on a substrate that are separated and used for the evaluation of different materials or process parameters. The SIR may have any convenient shape, e.g., circular, rectangular, elliptical, wedge-shaped, etc. In the semiconductor field, a region may include, for example, a test structure, single die, multiple dies, portion of a die, or other defined portion of substrate. The SIRs can be formed using many different methods such as scribing, deposition through a shadow mask, deposition using isolated deposition heads, lithography, and the like. Where one region is processed at a time, adjacent regions are generally protected from any exposure that would alter the substrate surface in a measurable way. Site isolation may provide complete isolation between regions or relative isolation between regions.

As used herein, "sputter gun" and "deposition head" are equivalent and used interchangeably to describe hardware, assembly, and apparatus used to perform PVD (e.g. sputtering) in a process chamber.

FIG. 1 is a schematic diagram of device development using primary, secondary, and tertiary screening methods that include HPC processing and may also include conventional processing. The diagram 100 illustrates how the selection of a subset of the most promising candidates at each stage decreases the relative number of combinatorial processes that need to be run in the next stage. Generally, a large number of processes are performed during a primary screening stage. Based on the primary-screening results, a subset of promising candidates is selected and subjected to a secondary screening stage. Based on the secondary-screening results, a smaller subset of promising candidates is selected and subjected to a tertiary screening stage, and so on. In addition, feedback from later stages to earlier stages can be used to refine the success criteria and provide better screening results.

For example, thousands of materials may be evaluated during a materials discovery stage 102, a primary screening stage. Techniques for this stage may include, e.g., dividing substrates into coupons and depositing materials on each of the coupons. Materials, deposition processes, or both may vary from coupon to coupon. The processed coupons are then evaluated using various metrology tools, such as electronic testers and imagers. A subset of promising candidates is advanced to the secondary screening stage, materials and process development stage 104.

Hundreds of materials (i.e., a magnitude smaller than the primary stage) may be evaluated during the materials and process development stage 104, which may focus on finding the best process for depositing each of the candidate materials. A subset of promising candidates is selected to advance to the tertiary screening stage, process integration stage 106.

Tens of material/process pairs may be evaluated during the process integration stage 106, which may focus on integrating the selected processes and materials with other processes and materials. A subset of promising candidates is selected to advance to device qualification stage 108.

A few candidate combinations may be evaluated during the device qualification stage 108, which may focus on the suitability of the candidate combinations for high volume manufacturing. These evaluations may or may not be carries out on full-size substrates and production tools. Successful candidate combinations proceed to pilot manufacturing stage 110.

The schematic diagram 100 is an example. The descriptions of the various stages are arbitrary. In other embodiments of HPC, the stages may overlap, occur out of sequence, or be described or performed in other ways.

HPC techniques may arrive at a globally optimal process sequence by considering the interactions between the unit manufacturing processes, the process conditions, the process hardware details, and material characteristics of components. Rather than only considering a series of local optima for each unit operation considered in isolation, these methods consider interaction effects between the multitude of processing operations, influenced by the order in which they are performed, to derive a global optimum sequence order.

HPC may alternatively analyze a subset of the overall process sequence used to manufacture a device; the combinatorial approach may optimize the materials, unit processes, hardware details, and process sequence used to build a specific portion of the device. Structures similar to parts of the subject device structures (e.g., electrodes, resistors, transistors, capacitors, waveguides, or reflectors) may be formed on the processed substrate as part of the evaluation.

While certain materials, unit processes, hardware details, or process sequences are varied, other parameters (e.g., composition or thickness of the layers or structures, or the unit process action such as cleaning, surface preparation, deposition, surface treatment, or the like) are kept substantially uniform across each discrete region of the substrate. Furthermore, while different materials or unit processes may be used for corresponding layers or steps in the formation of a structure in different regions of the substrate, the application of each layer or the use of a given unit process may be substantially consistent among the different regions. Thus, aspects of the processing may be uniform within a region (inter-region uniformity) or between regions (intra-region uniformity), as desired.

The result is a series of regions on the substrate that contain structures or unit process sequences that have been uniformly applied within that region or, as applicable, across different regions. This process uniformity allows comparison of the properties within and across the different regions so that the variations in test results are due to the intentionally varied parameter (e.g., material, unit process, unit process parameter, hardware detail, or process sequence) and not to a lack of process uniformity. The positions of the discrete regions can be defined as needed, but are preferably systematized for ease of tooling and design of experiments. The number, location, and variants of structures in each region preferably enable valid statistical analysis of test results within and between regions.

Figure 2:
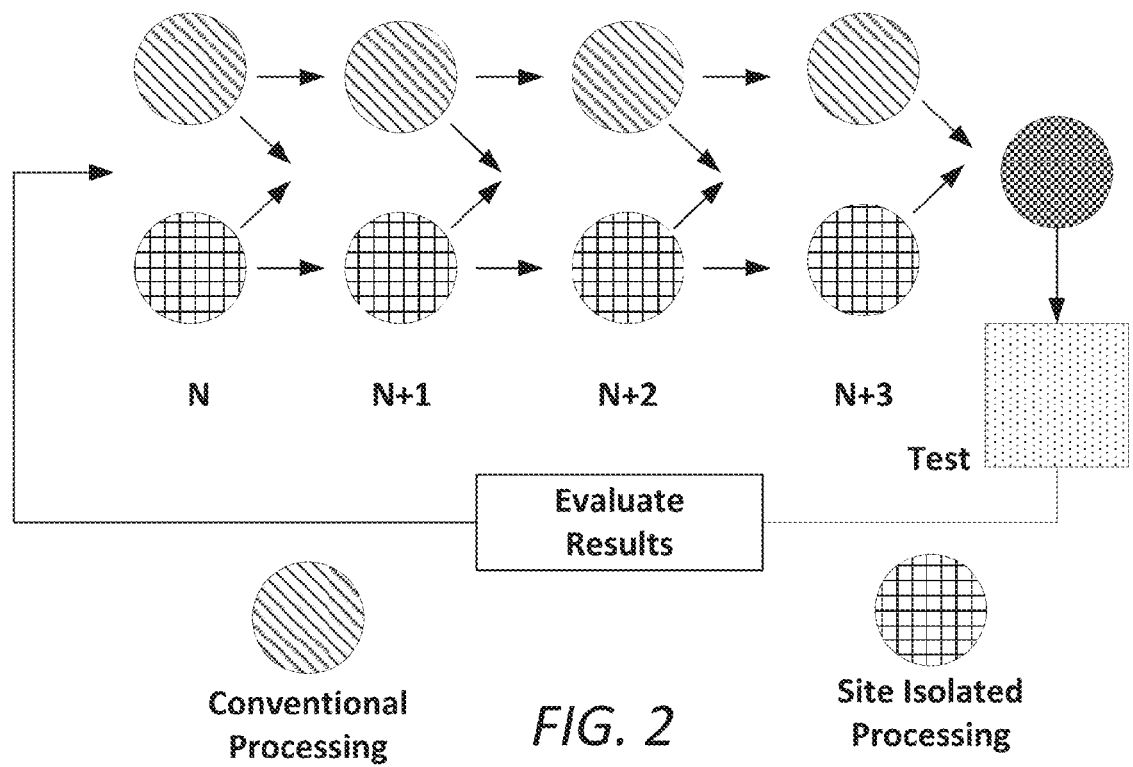
FIG. 2 is a simplified schematic diagram illustrating a general methodology for combinatorial process sequence integration that includes site-isolated processing, conventional processing, or both.

FIG. 2 is a simplified schematic diagram illustrating a general methodology for combinatorial process sequence integration that includes site-isolated processing, conventional processing, or both. In one embodiment, the substrate is initially processed using conventional process N, and then processed using site isolated process N+1. During site isolated processing, an HPC module may be used, such as the HPC module described in U.S. Pat. No. 8,084,400. The substrate can then be processed using site isolated process N+2, and thereafter processed using conventional process N+3. Testing is performed and the results are evaluated. The testing can include physical, chemical, acoustic, magnetic, electrical, optical, etc. tests. From this evaluation, a particular process from the various site isolated processes (e.g. from steps N+1 and N+2) may be selected and fixed so that additional combinatorial process sequence integration may be performed using site isolated processing for either process N or N+3. For example, a next process sequence can include processing the substrate using site isolated process N, conventional processing for processes N+1, N+2, and N+3, with testing performed thereafter.

Various other combinations of conventional and combinatorial processes can be included in the processing sequence. The combinatorial process sequence integration can be applied to any desired segments and/or portions of an overall process flow. Characterization can be performed after each process operation and/or series of process operations within the process flow as desired. Furthermore, the flows can be applied to entire monolithic substrates, or portions such as coupons.

Parameters which can be varied between site-isolated regions include, but are not limited to, process material amounts, reactant species, process temperatures, process times, process pressures, process flow rates, process powers, reagent compositions, the rates at which the reactions are quenched, atmospheres in which the processes are conducted, order in which materials are deposited, hardware details including gas or liquid distribution assemblies, etc. These process parameter examples are not an exhaustive list; numerous other process parameters used in device manufacturing may also be varied.

Within a region, the process conditions may be kept substantially uniform, in contrast to gradient processing techniques which rely on the inherent non-uniformity of the material deposition. That is, each site-isolated region may be processed in a substantially consistent and substantially uniform way, even though the materials, processes, and process sequences may vary from region to region over the substrate. Thus, the testing will find optima without interference from process variation differences between processes that are meant to be the same. Regions may be contiguous, or may overlap, or may be surrounded by unprocessed margins. Where regions are contiguous or overlapping, the materials or process interactions in the overlap may be uncertain. However in some embodiments at least 50% of the area within a region is uniformly processed and all testing can be done in that uniform area. Experiments may be designed to allow potential overlap only between materials or processes that will not adversely affect the result of the tests.

Combinatorial processing can be used to determine optimal processing parameters (e.g., time, concentration, temperature, stirring rate, etc.) of wet processing techniques such as wet etching, wet cleaning, rinsing, and wet deposition techniques (e.g., electroplating, electroless deposition, chemical bath deposition, dip coating, spin coating, and the like).

Figure 3:
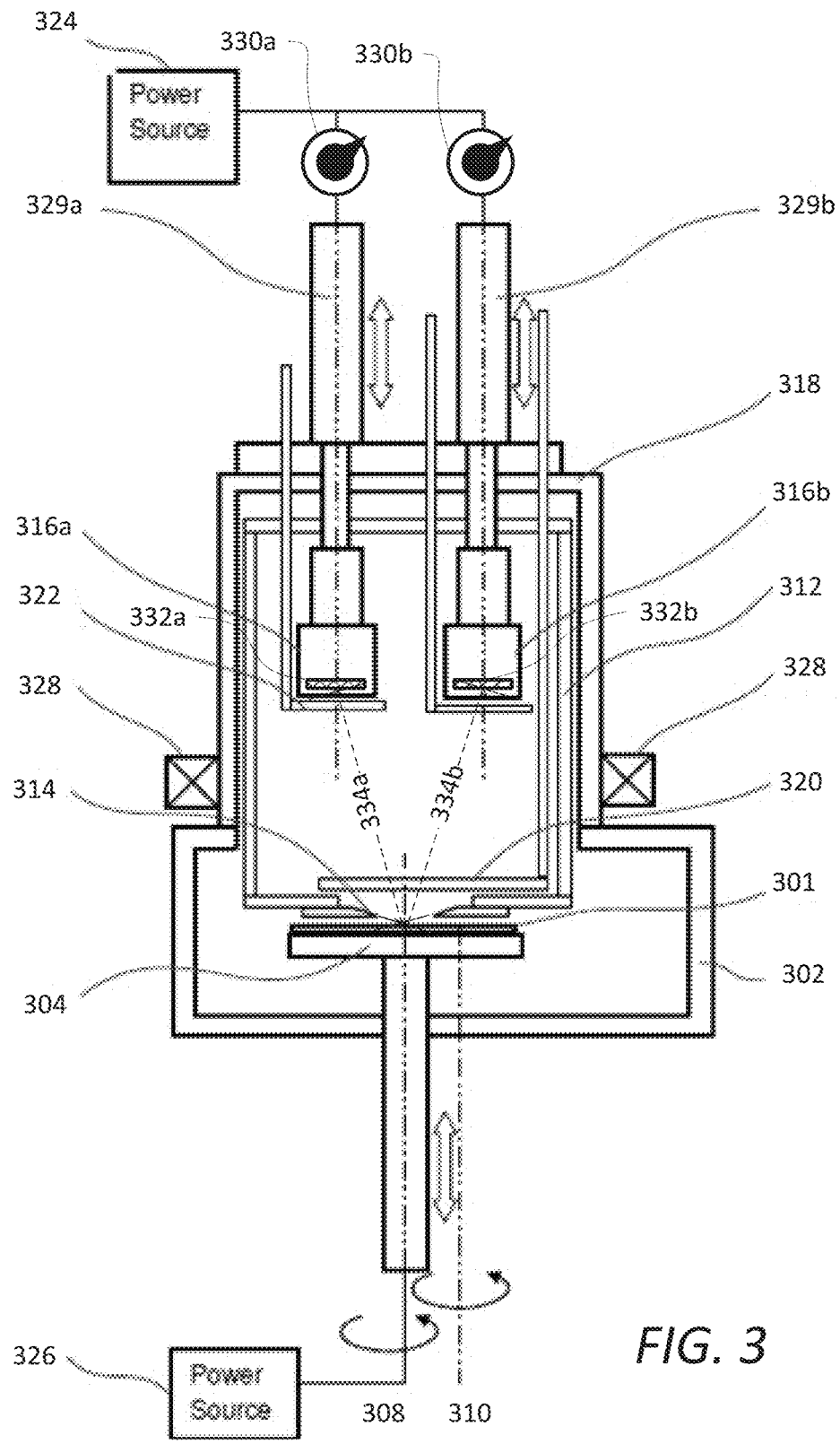
FIG. 3 is a block diagram of an example dual-target PVD process chamber.

FIG. 3 is a block diagram of an example dual-target PVD process chamber. Other types of PVD chambers may alternatively be used. Further details on chamber examples can be found in U.S. Pat. No. 8,039,052 filed 27 Dec. 2007 with a priority date of 6 Sep. 2007, and U.S. patent application Ser. No. 12/027,980 filed 7 Feb. 2008 with a priority date of 5 Sep. 2007, which are entirely incorporated by reference herein for all purposes.

The illustrated chamber includes a bottom chamber portion 302 and a top chamber portion 318. A substrate support 304 is configured to hold a substrate 301 in the bottom chamber portion 302. Substrate support 304 may include a vacuum chuck, an electrostatic chuck, or other known substrate support mechanisms. Substrate 301 may be any suitable size, shape, and material, and may include pre-existing layers or structures.

Substrate support 304 may be configured to rotate around its own central axis 308 ("rotation" axis), and revolve around a displaced axis 310 ("revolution" axis). Alternatively, other mechanisms for lateral motion, such as XY tables, may be used. In addition, substrate support 304 may move in a vertical direction. Any known drive mechanisms, including but not limited to magnetic drives, linear drives, worm screws, lead screws, and differentially pumped rotary feeds, may provide the motion. In addition, substrate support 304 may include heating and or cooling to control the temperature of substrate 301. Additionally or alternatively, the temperature of the chamber may be controlled by controlling the temperature of the chamber walls or some other component.

The chamber in FIG. 3 includes two sputter guns 316a and 316b (collectively "416a-b") housed in top chamber portion 318. Any other practical number of sputter guns (e.g., 1, 3, 3 or more) may alternatively be included. Each sputter gun holds a target 332a or 332b (collectively "432a-b") made of a material to be deposited on substrate 301. Their compositions may differ from each other. During deposition, targets 332a-b are bombarded by energetic particles, such as ions from a plasma or other ion source. Ions striking targets 332a-b initiate collision cascades in the target that result in ejection of atoms or molecules of the target material. The ejected target material is deposited on an exposed surface of substrate 301.

The sputter guns 316a-b may be vertically movable to be lifted from the slots of the shield. Arm extensions 329a and 329b (collectively "329a-b") may be attached to a drive, e.g., lead screw, worm gear, etc. to vertically move sputter guns 316a-b toward or away from top chamber portion 318. Alternatively or additionally, pivotal attachment to arm extensions 329a-b may adjust the tilt of the sputter guns relative to a vertical axis. In some embodiments, one or more of the sputter guns 316a-b are tilted so that a normal reference line 334a or 334b extending from a planar surface of target 332a or 332b intersects substrate 301 near the center of an exposed area, e.g., the area exposed by aperture 314. Alternatively, a sputter gun may be tilted to aim the target at an outer periphery of the exposed substrate area. In some embodiments, the tilt angle may be varied to accommodate variations of target size, target-to-substrate spacing, target material, process power/pressure, and the like. Each sputter gun may also include a gun shutter 322 to isolate its target 332a or 332b when deposition from that target is not desired, and/or to cover the opening when sputter guns 316a-b are lifted.

Power source 324 provides power for sputter guns 316a-b. For example, power source 324 may supply direct current (DC) continuous power, DC pulsed power, radio frequency (RF) power, or DC-RF imposed power. Power source 326 provides power to bias the substrate support 304. Power sources 324 and 326 may be controlled by a controller (not shown). In some embodiments, the output of the power source 326 is synchronized with the output of power source 324. The power to each of the sputter guns 316a and 316b may be independently controlled by individual power controllers 330a and 330b. Their illustrated positions are merely schematic; they are not restricted to any particular physical position on or off chamber 300.

Top chamber portion 318 may include a process kit shield 312 to confine plasma generated by sputter guns 316a-b to a confinement region over a portion of substrate 301. Sputtered material is deposited on the portion of substrate 301 under aperture 314 in the base of process kit 312. An aperture shutter 320 may be movable to partially or wholly cover aperture 314, thereby further confining or preventing deposition on substrate 301. In some embodiments, process kit shield 312 or a section containing aperture 314 may be movable within the chamber or removable from the chamber. In some embodiments, aperture 314 may contribute to the definition or isolation of a site-isolated region.

An auxiliary magnet 328 may be disposed around an external periphery of the chamber between the bottom surfaces of sputter guns 316a-b and the top surface of substrate support 304. In some embodiments auxiliary magnet 328 may be proximate to, or even integrated with, substrate support 304. Auxiliary magnet 328 may be a permanent magnet or an electromagnet. In some embodiments, auxiliary magnet 328 improves ion guidance as the magnetic field above substrate 301 is re-distributed or optimized, or provides more uniform distribution of charged species over an exposed portion of the substrate.

If substrate temperature is controllable over a sufficient range, both sputter deposition and annealing may be performed in the same process chamber. Alternatively, sputter deposition may be done in one chamber and the substrate may be moved to another chamber for annealing.

Figure 4A:
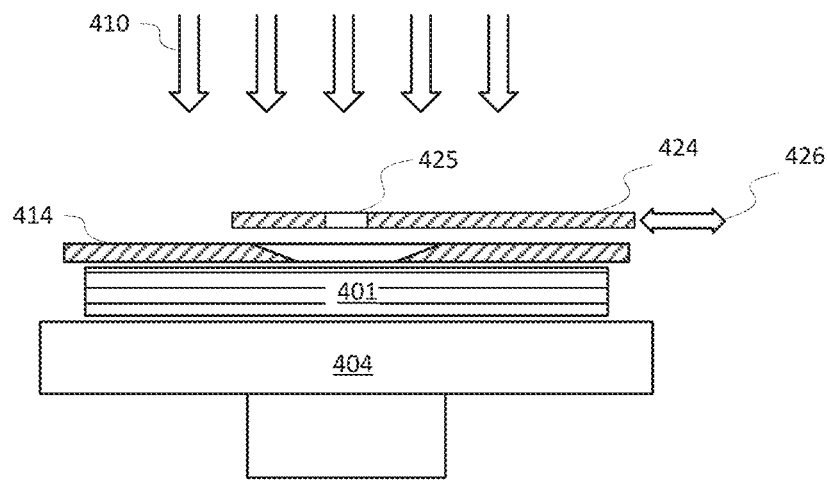
FIGS. 4A and 4B are block diagrams of a substrate holder associated with dual apertures of different size in a process chamber.
Figure 4B:
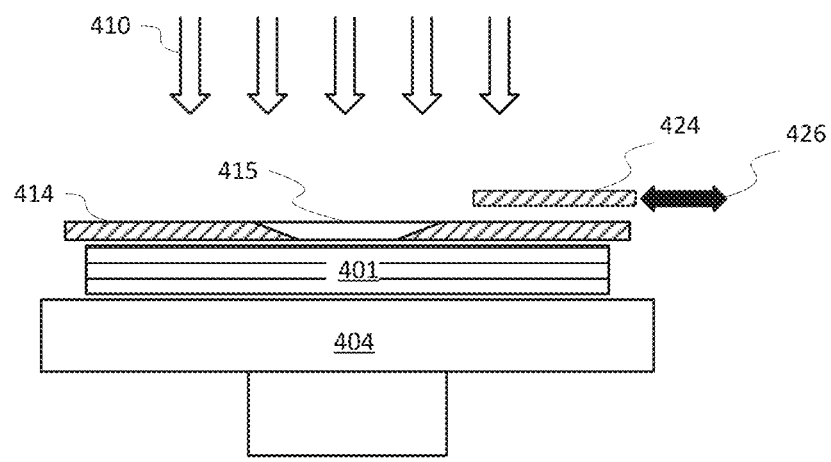

FIGS. 4A and 4B are block diagrams of a substrate holder associated with dual apertures of different size in a process chamber. The dual apertures 414 and 424 allow structures of different lateral sizes to be formed on the substrate. Substrate 401 rests on substrate holder 404 in the path of impinging deposition material 410. Shutter aperture 424 is movable by (schematically represented) motion actuator 426, which may either translate or rotate shutter aperture 424. When shutter aperture 424 is in the position of FIG. 4A, it combines with shield aperture 414 to restrict the access of impinging material 410 to only the area of the substrate exposed under smaller opening 425. When shutter aperture 424 is moved to the position of FIG. 4B, aperture 414 becomes the most restrictive aperture and impinging material 410 may reach the substrate anywhere within larger opening 425. With this type of arrangement, subsequent depositions or treatments may be applied to either the area of the substrate under larger opening 415, or to a smaller area of the substrate under smaller opening 425, by using motion actuator 426 to move shutter aperture 424 to the corresponding position. For example, the smaller opening may be 10-40 mm wide and the larger opening may be 25-75 mm wide (but wider than the small opening).

Figure 5A:
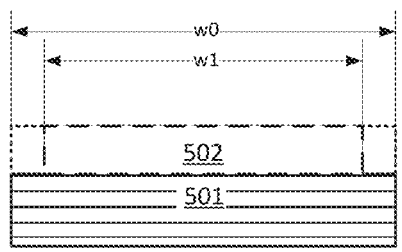
FIGS. 5A-5E demonstrate the fabrication of test structures for candidate barrier and seed layers.

FIGS. 5A-5E demonstrate the fabrication of test structures for candidate barrier and seed layers. The layers are deposited on differently sized areas by using a dual-aperture system like that in FIG. 4, or by any other suitable method. In FIG. 5A, substrate 501 may or may not have additional layers or structures already formed. Optionally, a dielectric layer 502 may be formed on substrate 501. For example, dielectric layer 502 may be $SiO_2$, some other oxide, or some other dielectric typical of an ILD. Dielectric layer 502 may be a uniform "blanket" layer over the entire substrate width $w_0$, or may be confined to a region of width $w_1$ (e.g., the width of a site-isolated region or "SIR"), or may be some intermediate width. Dielectric layer 502 may be the same material formed by the same process under the same conditions for every SIR on the substrate, or the material, formation process, or process conditions may differ between at least two of the SIRs.

Figure 5B:
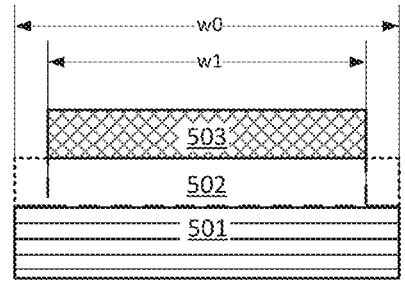

In FIG. 5B, a barrier layer 503 is formed on dielectric layer 502 (or directly on the substrate if layer 502 is not present). For example, barrier layer 503 may be a metal, a metal alloy, a metal nitride, or a stack of two or more different materials. Barrier layer 503 may be confined to a region of width $w_1$ (e.g., the width of a site-isolated region or "SIR") as shown, such as when its properties are being varied between different SIRs. However, if it is being held constant while some other layer is varied, barrier layer 503 may be a uniform "blanket"

layer over the entire substrate width $w_0$, or may be some intermediate width. Likewise, barrier layer 503 may be the same material formed by the same process under the same conditions for every SIR on the substrate, or its material, formation process, or process conditions may differ between at least two of the SIRs.

In some embodiments, barrier layer 503, with or without dielectric layer 502, may constitute the entire test structure. For example, barrier layer 503 may be combinatorially varied and the electrical or crystalline properties compared before and/or after annealing. As another example, either dielectric layer 502 or barrier layer 503 may be combinatorially varied and the concentration of one or more chemical components measured as a function of depth; e.g., if the dielectric layer is an oxide and the barrier layer is not, the amount of oxygen in the barrier layer after annealing may indicate the barrier layer's effectiveness in blocking oxygen diffusion.

Figure 5C:
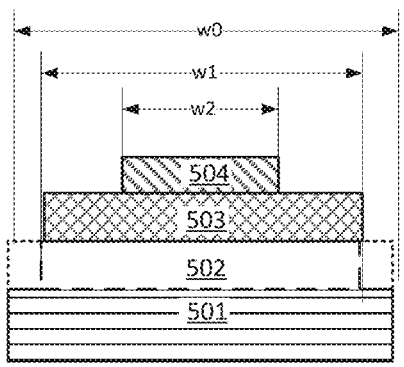

In FIG. 5C, a seed layer 504 has been added to the test structure. Its width may be $w_2<w_1$ to allow for complete encapsulation by an overlying oxygen-barrier layer of width $w_1$. For example, barrier layer 503 may be sputtered through a larger opening such as opening 415 in the shield aperture 414 of FIG. 4B, while seed layer 504 may be sputtered through a smaller opening such as opening 425 in the shutter aperture 415 of FIG. 4A.

Seed layers are often formulated to improve the adhesion or nucleation of an overlying interconnect metal Seed layers are often thin (<5 nm), although some may be up to 20 nm thick. In some experiments, seed layers may be varied in thickness (e.g., up to 40 nm) to evaluate at what seed-layer thicknesses the adhesion and other properties may change. Materials for seed layers may be metals (in some cases, the same metal as the interconnect), alloys, or other conductive materials. Seed layer 504 may be the same material formed by the same process under the same conditions for every SIR on the substrate, or its material, formation process, or process conditions may differ between at least two of the SIRs.

In some embodiments, seed layer 504 and barrier layer 503, with or without dielectric layer 502, may constitute the entire test structure. Any of the layers may be combinatorially varied in two or more SIRs. Then, for example, the seed layer may be inspected for agglomeration after annealing. As another example, the layer composition may be analyzed after annealing to look for diffusion of material both from and to the dielectric layer and the seed layer. As an additional example, the electrical properties of any or all of the layers may be measured before and after annealing (e.g., to check for any changes that might be due to diffusion).

Figure 5D:
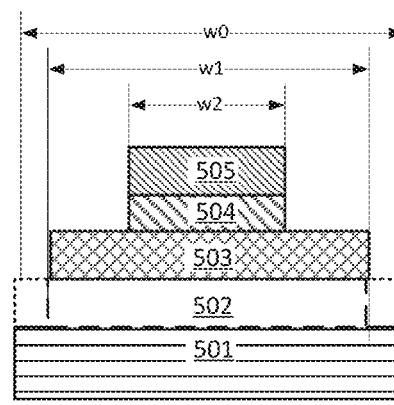

In FIG. 5D, a conductive layer 505 is added to the test structure. The conductive layer may be, for example, the material being used for interconnects (e.g., copper). Its thickness may be, e.g., 30-50 nm. It may be formed over seed layer 504, or the seed layer may be omitted and the conductive layer may be formed directly over barrier layer 503. In some embodiments, the width of the conductive layer is $w_2<w_1$. In some embodiments, the structure of FIG. 5D may be the entire test structure, and any of the layers 502, 503, 504, or 505 may be combinatorially varied.

Figure 5E:
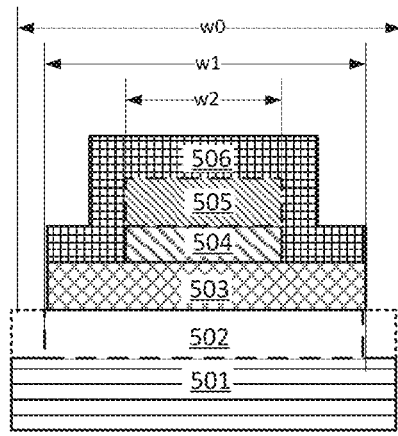

In FIG. 5E, a cap layer 506 is added to the test structure. The cap layer may be, for example, the same material or multilayer stack as barrier layer 503, a mirror image of barrier layer or stack 503, or a different material. Cap layer 506 may be 3-10 nm thick, formed over either or both of seed layer 504 and conductive layer 505. In some embodiments, the width of the cap layer is $w_1$, so that the barrier layer and the cap layer together encapsulate the seed layer, conductive layer, or both to keep out external oxygen and keep it from affecting oxygen-diffusion measurements. For example, a shutter aperture may be moved away and the cap may be deposited through a larger shield aperture. In some embodiments, the structure of FIG. 5E may be the entire test structure, and any of the layers 502, 503, 504, 505, or 506 may be combinatorially varied. In embodiments where cap layer 506 is not combinatorially varied, it may be formed as a blanket layer over the entire substrate or over a part of the substrate larger than an SIR.

Figure 6:
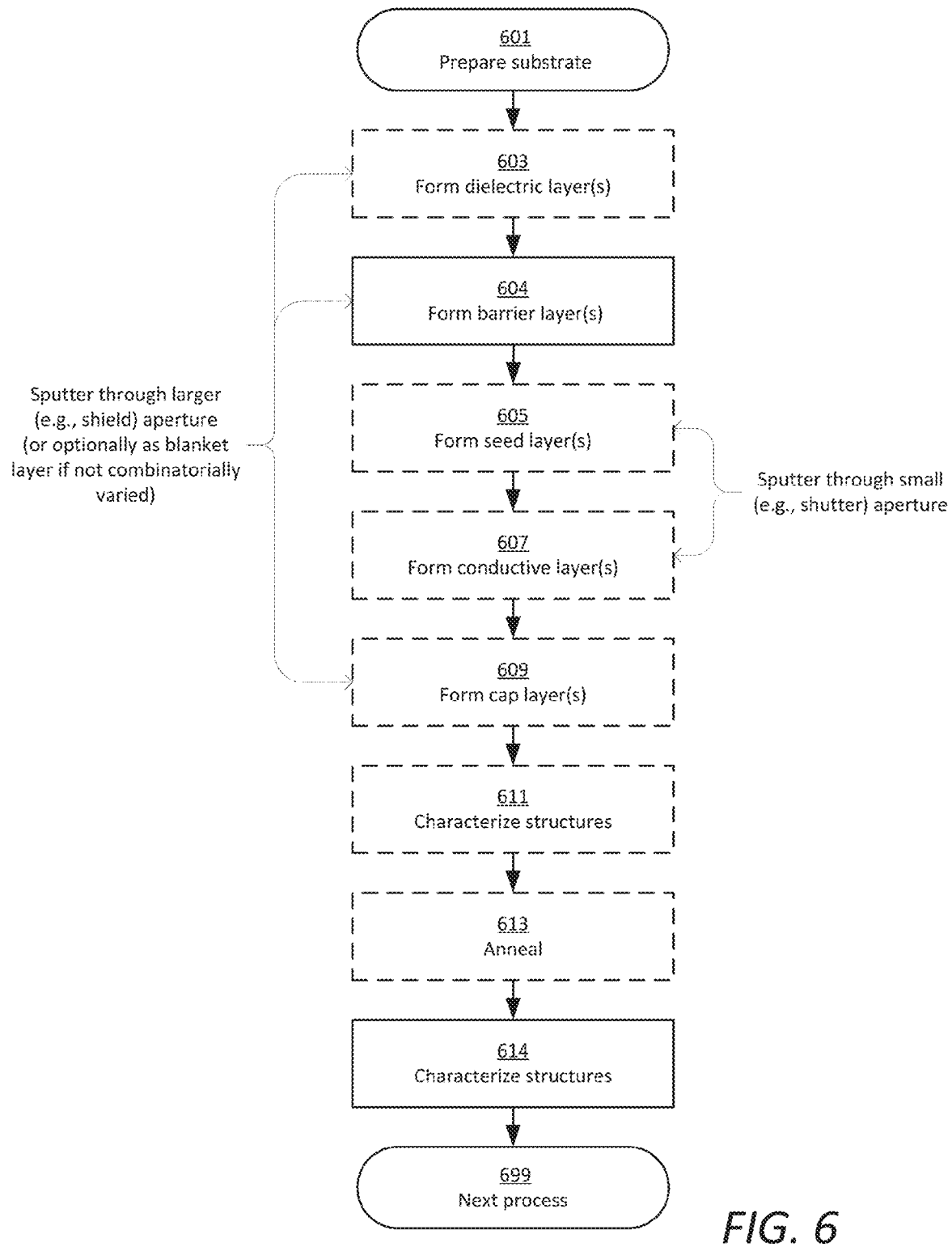
FIG. 6 is a flowchart of an example process for combinatorially screening layers used in interconnects.

FIG. 6 is a flowchart of an example process for combinatorially screening layers used in interconnects. Step 601 of preparing the substrate may include cleaning, degassing, or the formation of underlying layers or structures. Optional step 603 of forming one or more dielectric layers may use PVD (e.g., sputtering an oxide from an oxide target, or sputtering from a semiconductor or metal target in an oxidizing atmosphere), or any other method such as chemical vapor deposition (CVD), atomic layer deposition (ALD), or thermal oxidation. The dielectric layer may be identical in all the SIRs or may vary between SIRs, depending on the purpose of the experiment.

Step 604 of forming a barrier layer or barrier stack may include, for example, sputtering of one or more metals, alloys, or nitrides from one or more targets. For example, if alloys of the same constituent elements in different ratios are being screened for use as barrier layers, separate targets made of each of the constituents may be co-sputtered, and the ratio varied between the SIRs by varying the power, distance or angle of the target. If the barrier layer is being combinatorially varied, it may be sputtered through a large aperture as discussed with reference to FIG. 4. If it is not combinatorially varied (e.g., if different seed layers are being compared on a constant barrier layer) the barrier layer may be a blanket layer.

Optional step 605 of forming a seed layer may involve sputtering or co-sputtering options similar to barrier layer formation 604. Seed layer formation 605 may be combinatorially varied. As with combinatorial variation of barrier layer formation 604, the target material, pressure, ambient composition, target distance, or target angle may differ between at least two of the SIRs. In some embodiments, the seed layers only cover part of the barrier layer. For example, the seed layer may be sputtered through a shutter aperture smaller than the aperture used to deposit the barrier layer. Optional step 605 of forming a conductive layer may also include sputtering or co-sputtering through an aperture smaller than the one used for the barrier layer. The conductive layer may be the same size as the seed layer, or it may be smaller.

Optional step 609 of forming a cap layer over the conductive layer, seed layer or both may include sputtering or co-sputtering options similar to barrier layer formation 604. Cap layer formation 609 may be combinatorially varied. As with combinatorial variation of barrier layer formation 604 and seed layer formation 605, the target material, pressure, ambient composition, target distance, or target angle may differ between at least two of the SIRs. To completely encapsulate the metals of the conductive layer, seed layer or both, the cap layer may be sputtered through a larger aperture than the seed and/or conductive layer. If the cap layer is not being combinatorially varied, it may be deposited as a blanket layer.

Note that using the apertures in the PVD chamber to define the sputtered areas of the various layers requires fewer steps than other approaches to making layers of different lateral extents (e.g., etching the layers to different widths after depositing them). Moreover, all these steps may optionally be done in the same chamber without a vacuum break. This accelerates the screening process and removes extra variables (e.g., the effects of wet or dry etchants and contaminants picked up when switching chambers). Note also that treatments such as cleaning or passivation may optionally be done between any of the steps.

Optional step 611 of characterizing one or more of the layers before annealing the structures may involve measuring electrical properties, crystalline morphology, chemical composition, surface roughness, or any other quantity related to performance of interconnects and their barrier layers. Optional step 613 of annealing the structures may involve a rapid thermal anneal (high temperature for a few minutes), a slow bake (lower temperature for hours or days) or an intermediate process. Annealing 613 may be combinatorially varied by cleaving the substrate into two or more coupons and subjecting each coupon to different annealing conditions.

In step 614, the structures are characterized and the results of the different SIRs are compared with each other and with expected results for acceptable barrier layers or interconnects. The most promising candidates are selected for a further round of screening in next process 699.

Example

Screening of Ta—Ti Barriers and Cu—Mn Seed Layers

A series of HPC screening experiments investigated (1) whether a thinner layer or stack including a Ta—Ti alloy could replace a thicker TaN/Ta stack as a barrier between a copper interconnect and a $SiO_2$ ILD, and (2) whether adding 1.5-2.5% manganese (Mn) to a copper seed layer could reduce diffusion or promote adhesion of thin (e.g., <10 nm) copper layers. The structures were fabricated on Si substrates with $SiO_2$ dielectric layers in a four-target PVD chamber. Separate, independently controllable sputter guns applied DC power to a Ta target, a Ti target, a Cu target, and a Cu—Mn target (alternatively, a separate Mn target could have been used and co-sputtered with the Cu to make CuMn) about 320 mm from the substrate. The structures were sputtered onto the substrate through a larger shield aperture (for barrier and cap layers) and a smaller shutter aperture (for the seed and conductive layers).

Figure 7A:
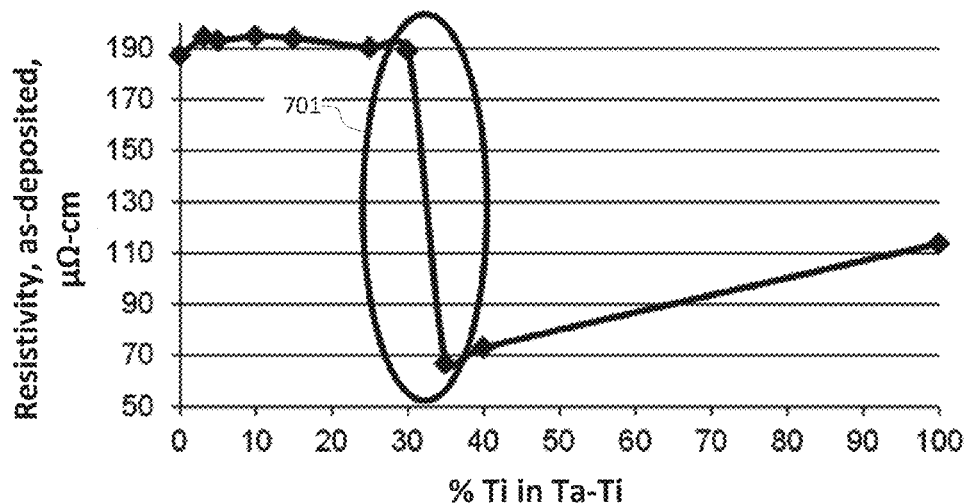

FIGS. 7A-7I are examples of results from HPC screening experiments. FIG. 7A plots the resistivity of Ta—Ti barrier layers co-sputtered from separate Ta and Ti targets on different SIRs. The atomic percentage (at %) of Ti was combinatorially varied from about 3% to about 100% by adjusting the DC power independently at the Ta and Ti targets. For example, for Ta—Ti with 30% Ti the Ta target power was about 205 W on a 2" diameter active area (~4.6 $W/cm^2$) and the Ti target power was about 175 W on a 2" diameter active area (~4 $W/cm^2$). For 40% Ti the Ta target power was about 180 W on a 2" diameter active area (~4.1 $W/cm^2$) and the Ti target power was about 239 W on a 2" diameter active area (~5.4 $W/cm^2$). After deposition, the compositions were measured by both XRF and RBS; the measurements agreed well with each other and with the intended target ratios. Thicknesses of the barrier layers were 2-2.1 nm as measured by X-ray reflectometry ("XRR"). At Ti % up to about 30, the resistivity was high (~190 $\mu\Omega$-cm) and nearly constant. In interval 701 between about 30% and about 36% Ti, the resistivity dropped abruptly to a minimum, then began to rise again for larger % Ti. This screening showed that more than 30% Ti was needed to produce a low-resistivity alloy, and that the resistivity minimum was around 35%. However, even the "high-resistivity" alloys were less resistive than TaN/Ta (~280 $\mu\Omega$-cm).

Figure 7B:
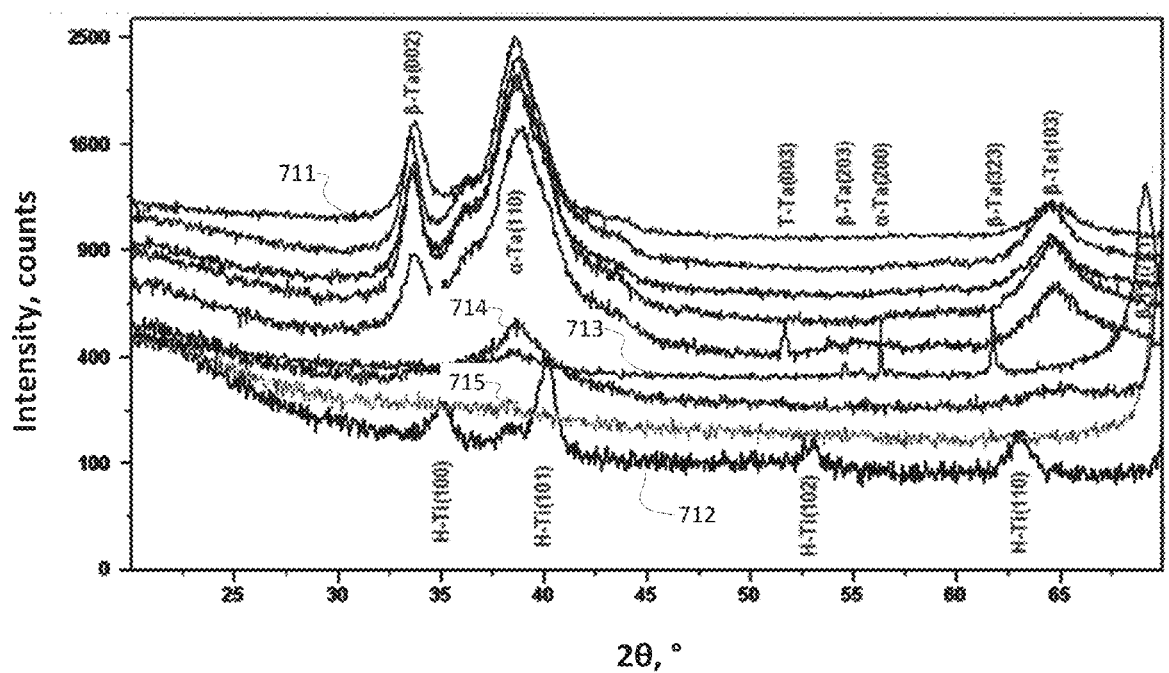

In FIG. 7B, XRD measurements of the various Ta—Ti barrier layers showed that the resistivity drop corresponds to a phase transformation. Curve 711 (with no discernible Ti peaks) represents 3% Ti, and curve 712 (with no discernible Ta peaks) represents 100% Ti. The curves immediately below curve 711 (5, 10, 15, and 25% Ti in descending order) show the expected gradual decline in Ta peaks and eventual emergence of some Ti peaks, as expected. Curves 713 (30% Ti), 714 (36% Ti), and 715 (40% Ti), corresponding to the resistivity drop, do not have the shape of a straightforward superposition of Ta and Ti and appear dissimilar to the other curves.

Figure 7C:
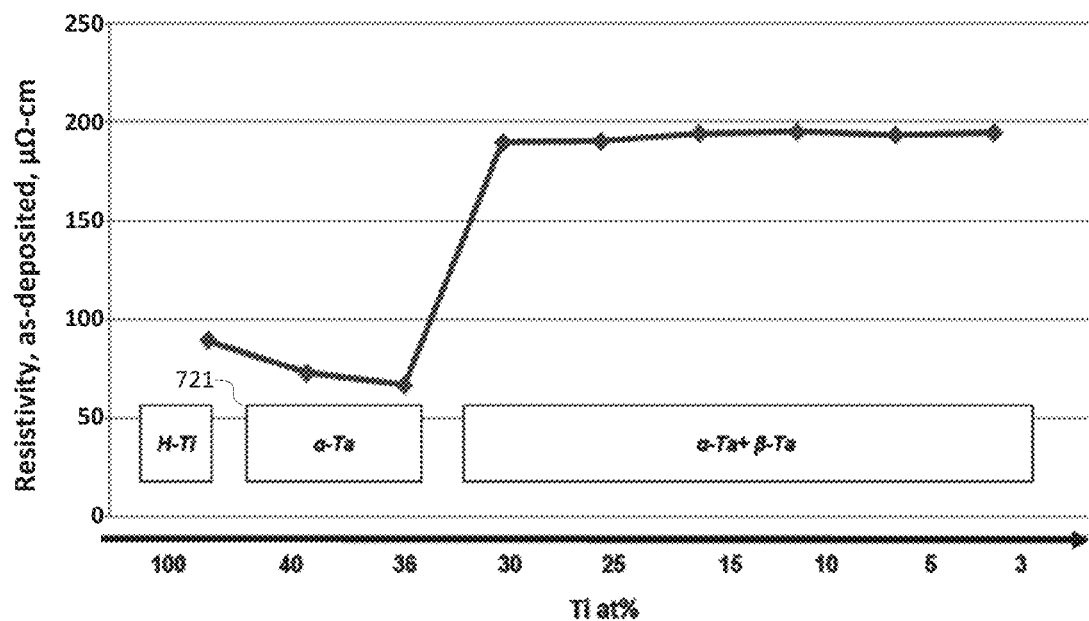

In FIG. 7C, as-deposited resistivity is plotted vs. decreasing Ti content, and the corresponding dominant peaks of the XRD measurement are added as labels 721 underneath the resistivity curve.

Figures 7D, 7E, 7F:
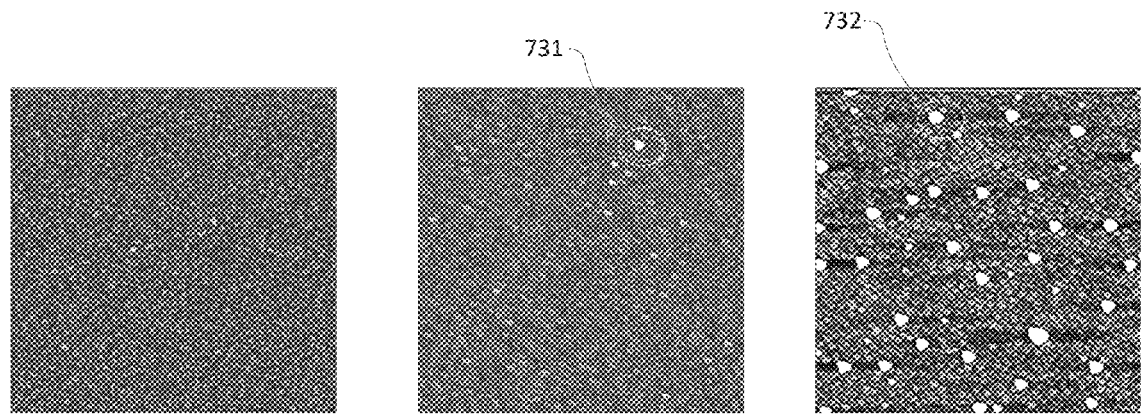

Barrier layers between metal interconnects and oxide ILD materials often need to keep oxygen out of the interconnect, as well as keeping metal inside the interconnect. Defects attributable to diffused oxygen may be visible in the surface of a layer, for example in an AFM image. In another experiment, combinatorially varied Ta—Ti barriers were co-sputtered on $SiO_2$ dielectric layers and compared with a "control" standard TaN/Ta stack. FIGS. 7D-F are AFM images with contrast and sharpness manipulated to discernibly display their features in black-and-white with minimal grayscale. FIG. 7D is the control TaN/Ta layer (actually "Ta/TaN" when used as a cap, to put the Ta in contact with the seed layer). The uniformity of the image shows virtually no evidence of oxygen diffusion. FIG. 7E, the Ta—Ti with 3% Ti, shows only a little oxygen diffusion (e.g., large white speck 731). FIG. 7F, the Ta—Ti with 30% Ti, shows much more oxygen diffusion (e.g., large white specks 732).

Interconnect materials preferably form contiguous films; gaps in coverage may cause open-circuit faults. As Cu layers become thinner, annealing may cause them to agglomerate (form islands separated by gaps). HPC experiments with different Cu conductive-layer thicknesses on standard TaN/Ta showed that Cu thicknesses below about 20 nm will agglomerate if deposited on TaN/Ta and annealed at 350 C for 30 minutes. FIGS. 7G-H are AFM images with contrast and sharpness manipulated to discernibly display their features in black-and-white with minimal grayscale. FIG. 7G shows a 5 nm Cu film on TaN/Ta after the 30 min, 350 C anneal. Large agglomerated islands 741 are clearly visible. FIG. 7H shows a 5 nm Cu film on Ta—Ti (30% Ti) after the same anneal; smooth and contiguous, with no islands. This behavior was observed with all the Ta—Ti barriers that were investigated. This suggests that thin Cu has better adhesion to Ta—Ti than to TaN/Ta, which will become important as interconnect structures continue to scale down.

In another phase of the development, 1.5 nm-thick Ta—Ti barrier layers with varying % Ti were topped with seed layers; some with Cu seed layers and some with Cu—Mn seed layers. The resulting test structures were annealed for 30 min at various temperatures. The sheet resistance of the Ta—Ti barriers was measured before and after annealing, which was easily done since the barrier layers were not completely covered by the smaller-area seed layers.

FIG. 7I shows the change in sheet resistance plotted as a function of the anneal temperature. The desired result is that the barrier sheet resistance does not increase after annealing. Curve set 751 represents the Cu seed layers. All of them, regardless of % Ti, increased in sheet resistance after the 400 C anneal (and more so after the higher-temperature anneals). Curve set 752 represents the Cu—Mn seed layers. All of them, regardless of % Ti, retained their original sheet resistance after the 400 C anneal, but increased in sheet resistance after the 525 C anneal. This suggests that the Cu—Mn seed layer not only helps Ta—Ti barrier layers withstand 400 C annealing without losing conductivity, but may also enhance the diffusion-blocking function; changes in a layer's electrical properties (e.g., sheet resistance) after annealing may be a symptom of interdiffusion between layers.

Related HPC experiments showed that high-resistivity 2.5 nm-thick Ta—Ti barriers (<30% Ti) were more effective than TaN/Ta. 2 nm and 1.5 nm thicknesses were less satisfactory by themselves, but performed acceptably when paired with a Cu—Mn seed layer.

Although the foregoing examples have been described in some detail to aid understanding, the invention is not limited to the details in the description and drawings. The examples are illustrative, not restrictive. There are many alternative ways of implementing the invention. Various aspects or components of the described embodiments may be used singly or in any combination. The scope is limited only by the claims, which encompass numerous alternatives, modifications, and equivalents.

What is claimed is:

1. A method, comprising:
   defining a plurality of site-isolated regions on a substrate, wherein the substrate comprises a dielectric layer formed over each of the plurality of site-isolated regions;
   forming a first layer over the dielectric layer of each of the plurality of site-isolated regions, wherein the first layer comprises a tantalum-titanium alloy;
   forming a second layer over the first layer of each of the plurality of site-isolated regions, wherein the second layer comprises copper, and the dielectric layer, the first layer, and the second layer formed over each of the plurality of site-isolated regions jointly form a test structure;
   varying at least one process parameter of the forming of the first layer or the forming of the second layer between at least two of the site-isolated regions by at least 5%; and
   measuring a characteristic of the test structure formed over each of the plurality of site-isolated regions.

2. The method of claim 1, wherein at least one of the forming of the first layer and the forming of the second layer is performed by sputtering material from at least one of a plurality of targets, wherein said sputtered material passes through at least one aperture positioned between the substrate and the at least one of a plurality of targets.

3. The method of claim 1, wherein the atomic percentage of titanium in the tantalum-titanium alloy in the first layer of each of the test structures is at least about 30%.

4. The method of claim 2, wherein one of the plurality of targets comprises copper.

5. The method of claim 2, wherein one of the plurality of targets comprises tantalum, and one of the plurality of targets comprises titanium.

6. The method of claim 1, wherein the first layer comprises an oxide.

7. The method of claim 6, wherein the first layer comprises silicon dioxide.

8. The method of claim 3, wherein the varying of the at least one process parameter of the forming of the first layer or the forming of the second layer between at least two of the site-isolated regions comprises varying the atomic percentage of titanium in the tantalum-titanium alloy in the first layer.

9. The method of claim 8, wherein the atomic percentage of titanium in the tantalum-titanium alloy in the first layer of each of the test structures is between about 30% and about 40%.

10. The method of claim 9, wherein a thickness of the first layer is between about 2 nm and about 5 nm.

11. The method of claim 10, wherein a thickness of the second layer is between about 30 nm and about 50 nm.

12. The method of claim 2, wherein the forming of the first layer is performed by sputtering tantalum and titanium from the at least one of the plurality of targets, wherein said sputtered tantalum and titanium passes through a first aperture positioned between the substrate and the least one of the plurality of targets, and wherein the forming of the second layer is performed by sputtering copper from the at least one of the plurality of targets, wherein said sputtered copper passes through the first aperture and a second aperture positioned between the substrate and the at least one of the plurality of targets.

13. The method of claim 12, wherein the second aperture is coupled to an actuator, wherein the actuator is configured to move the second aperture.

14. The method of claim 1, wherein the measured characteristic comprises diffusion of copper.

15. The method of claim 1, wherein the measured characteristic comprises diffusion of oxygen.

16. The method of claim 1, further comprising forming a third layer between the first layer and the second layer of the test structure of each of the plurality of site-isolated regions.

17. The method of claim 16, wherein the third layer is a conductive layer.

18. A method, comprising:
   defining a plurality of site-isolated regions on a substrate;
   forming a dielectric layer above each of the plurality of site-isolated regions;
   forming a barrier layer above the dielectric layer of each of the plurality of site-isolated regions, wherein the barrier layer comprises a tantalum-titanium alloy with an atomic percentage of titanium of between about 30% and about 40%;
   forming a conductive layer above the barrier layer of each of the plurality of site-isolated regions, wherein the conductive layer comprises copper, and the dielectric layer, the barrier, and the conductive layer formed over each of the plurality of site-isolated regions jointly form a test structure;
   varying at least one process parameter of the forming of the barrier layer or the forming of the conductive layer between at least two of the site-isolated regions by at least 5%; and
   measuring a characteristic of the test structure formed over each of the plurality of site-isolated regions.

19. The method of claim 18, wherein the dielectric layer comprises silicon dioxide.

20. The method of claim 19, wherein a thickness of the barrier layer is between about 2 nm and about 5 nm, and a thickness of the conductive layer is between about 30 nm and about 50 nm.

* * * * *